United States Patent [19]

Barr et al.

[11] Patent Number: 4,732,973

[45] Date of Patent: Mar. 22, 1988

[54] ACTIVE SITE MODIFIED PROTEASE α-1-ANTITRYPSIN INHIBITORS

[75] Inventors: Philip J. Barr, Orinda; Robert A. Hallewell, San Francisco; Steven Rosenberg, Oakland, all of Calif.

[73] Assignee: Chiron Corporation, Emeryville, Calif.

[21] Appl. No.: 620,408

[22] Filed: Jun. 14, 1984

[51] Int. Cl.$^4$ ............................................. C07K 13/00
[52] U.S. Cl. .................................................... 530/350
[58] Field of Search ......................................... 530/350

[56] References Cited

FOREIGN PATENT DOCUMENTS 0155188  3/1985  European Pat. Off. .

OTHER PUBLICATIONS

Archives of Biochem. & Biophys. 188 (1978), 226–227.
The Journal of Biol. Chem. 254, 4022–4026 (1979).
PCT/WO86/00337, 16 Jan. 1986 Courtney.
The Journal of Biological Chem. 255, (1980), 3931–3934.
Angew Chem. Int. Ed. Engl. 20, (1981), 295–296.
Archives of Biochemistry & Biophys. 177, 552–560 (1976).
Biochim. et Biophys. Acta. 453 (1976), 257–261.

Primary Examiner—Delbert R. Phillips
Attorney, Agent, or Firm—Ciotti & Murashige, Irell & Manella

[57] ABSTRACT

Proteinaceous composition are provided which inhibit naturally occurring serine proteases. Particularly, an amino acid sequence analogous to human $\alpha_1$-antitrypsin is modified at the active site while maintaining protease inhibition. The methionine at the active site is substituted with an oxidatively stable amino acid, while other amino acids may also be changed, added or deleted, particularly at the termini.

The yeast strains AB103.1 (pCl/PH05ATi(Val) and AB110 (pCl/1GAPATi(Val) were deposited at the A.T.C.C. on June 18, 1984 and given Accession Nos. 20711 and 20712, respectively.

4 Claims, No Drawings

ACTIVE SITE MODIFIED PROTEASE α-1-ANTITRYPSIN INHIBITORS

BACKGROUND OF THE INVENTION

1. Field of the Invention

Proteases or peptidases have a wide range of activities, functions and specificities in vivo. The need to produce various polypeptides for specific functions, while controlling their lifetime is an important function of peptidases. Peptidases also serve to process various proteins, whereby leader sequences may be removed, hormones or other active polypeptides excised from a larger polypeptide or the like. An alternative method for controlling the enzymatic activity at a particular site or in a medium in a host is the production of a specific enzyme inhibitor. This strategy is employed with human leukocyte elastase, a serine protease. Leukocyte elastase is involved in the phagocytosis of pathogens in the lungs. Failure to inhibit the enzyme, so that native tissue is attacked, can result in pulmonary emphysema or acute respiratory distress syndrome.

The naturally occurring human $\alpha_1$-antitrypsin has a methionine at the active site for inhibition of many serine proteases, particulary elastase. Oxidation of the methionine to the sulfoxide substantially inactivates the inhibitory activity towards most serine proteases, but not human chymotrypsin.

The ability to inhibit an enzyme, either reversibly or irreversibly, has a wide variety of applications. For therapeutic purposes, the ability to protect a host from the degradative effects of elastase can provide protection from the diseases indicated above. In in vitro systems, there are also uses for inhibition. For example, in diagnostic assays, where one can modulate inhibition in relation to the presence or absence of a ligand, one can use the inhibition for a measurement of the presence or amount of the particular ligand. Furthermore, specific inhibitors can be used for titration of the enzyme, where only a non-specific substrate is available, for isolation and/or purification of an enzyme. Thus, novel enzyme inhibitors can have a wide variety of applications, both in vivo and in vitro.

2. Description of the Prior Art

Partial nucleotide sequences of $\alpha_1$-antitrypsin have been reported by Kurachi et al., *Proc. Natl. Acad. Sci. USA* (1981) 78:6826-6830 and Leicht et al., *Nature* (1982) 297:655-659. See also Suggs et al., *Proc. Natl. Acad. Sci. USA* (1981) 78:6613-6617; and Ish-Horowicz and Burke, *Nucleic Acids Research* (1981) 9:2989-2998. The existence of polymorphisms in $\alpha_1$-antitrypsin is reported by Fagerhol and Cox, *Adv. Hum. Genet.* (1981) 11:1-62. Beatty et al., *J. Biol. Chem.* (1980) 255:3931-3934, report that oxidation of $\alpha_1$-antitrypsin reduces serine protease inhibitory activity. Nakajima et al., ibid (1979) 254:4027-4032 show that a valine derivative is a human leukocyte elastase substrate. Travis and Salvesen, *Ann. Rev. Biochem.* (1983) 52:655-709, gives a review of $\alpha_1$-antitrypsin and its properties. See also copending application Ser. No. 609,540, filed May 11, 1984 abandoned.

SUMMARY OF THE INVENTION

Novel polypeptide serine protease inhibitors are provided, demonstrating enhanced storage and oxidative stability with high levels of inhibition. Efficient production of the inhibitors is obtained in yeast, where the polypeptide inhibitors may be isolated, purified and employed in a variety of ways.

DESCRIPTION OF THE SPECIFIC EMBODIMENTS

Novel DNA constructs are provided for expression of novel serine peptidase inhibitors which find use in vivo and in vitro applications. The peptidase inhibitors share a substantial identity with human $\alpha_1$-antitrypsin, while differing at the active site in having an oxidation-resistant amino acid, capable of simulating the inhibitory effect of methionine, and having from zero to five number percent of the other amino acids modified, deleted or added, usually not more than about ten amino acids, more usually not more than about five amino acids, from the naturally occurring wild-type $\alpha_1$-antitrypsin, where each deletion, substitution or addition is counted as one. The compositions are found to have inhibitory activity to human leukocyte elastase comparable to the naturally occurring $\alpha_1$-antitrypsin having methionine at the active site.

The polypeptide products of the subject invention may be glycosylated or non-glycosylated, usually non-glycosylated and are available using hybrid constructs involving combining DNA sequences from diverse sources. Hybrid polypeptides may be prepared which will generally range from about 350 to 500 amino acids. These polypeptides will, except for the modification of the methionine residue retain the $\alpha_1$-antitrypsin sequence for an oligopeptide sequence of at least about 10 amino acids, usually at least about 40 amino acids, and more usually at least about 80 amino acids, which sequence includes the active site of $\alpha_1$-antitrypsin and at least five amino acids flanking both sides of the active site. Where using the numbering of $\alpha_1$-antitrypsin as indicated in the Experimental, this will involve amino acids 290 to 394, more usually 310 to 390 and particularly 340 to 380. The non-$\alpha_1$-antitrypsin residues may be employed for immunogenic purposes, for modifying the characteristic of the inhibitory properties, or to provide a plurality of activities.

Fragments may also find use, particularly fragments involving at least about 20 amino acids, more usually at least about 30 amino acids, and preferably at least about 50 amino acids, and not more than about 200 amino acids where the fragments include the active site and for the most part the naturally occuring amino acids on each side of the active site, generally at least about ten amino acids on each side, more usually at least about 15 amino acids on each side, where the amino acids do not differ by more than ten number percent, more usually by not more than about five number percent from the wild-type sequence provided in the Experimental section. It should be understood that to the extent that naturally occurring alleles have been already isolated or may be isolated in the future, those sites in $\alpha_1$-antitrypsin where allelic variation is observed may also be varied in the subject polypeptides. Particularly, the residues of the sequence in the Experimental differing from those residues described by Carrell et al., *Nature* (1982) 298:329-334 and Bollen et al., *DNA* (1983) 2:255-264 may be modified with substantial retention of enzyme inhibition.

The DNA and polypeptide sequences of particular interest are set forth in the Experimental section, where the modified active site is indicated.

The substitution at the active site will be an oxidative-resistant L-amino acid of from three to six carbon atoms, preferably of from four to five carbon atoms, where the side chain may be hydrocarbon or hydroxy substituted hydrocarbon, preferably hydrocarbon, including alanine, valine, leucine, isoleucine, serine, and threonine, particularly valine.

The DNA constructs which are employed will usually involve an extrachromosomal element having a replication system recognized by at least one unicellular microorganism, such as a bacterium, e.g., E. coli, B. subtilis, etc.; fungi, particularly yeast, e.g., S. cerevisiae, S. pombe, S. carlsbergensis, etc.; or other organism, e.g., Streptomyces, Neurospora, or the like. Conveniently, there may be two replication systems, so that a shuttle vector is provided, so that during the preparation of the vector, the construction may be conveniently cloned in E. coli for enhancing the amount of material available and purification of the construct. Alternatively, the gene may be introduced into the host under conditions which result in integration, particularly in conjunction with a gene which provides for amplification, e.g., dihydrofolate reductase, metallothionein, etc.

The replication system may be obtained from either plasmids or viruses and may be derived from such plasmids as ColEl, e.g., pBR322, R-plasmid, e.g., pRK290, 2 μm plasmid, pJDB219, YEp4, YEp24, etc. Many of the replication systems are generally available and have been extensively described in the literature.

Usually the replication system will be available in combination with from zero to three, more usually from one to three genetic markers, structural genes which allow for selection of the host containing the replication system and marker, which combination will be referred to as a vector. The markers may allow for selection in one or more hosts or different markers may be used for the different hosts. The markers conveniently include biocide resistance, e.g., antibiotic resistance to streptomycin, penicillin, chloramphenicol, tetracycline, tunicamycin, kanamycin, etc.; heavy metals, e.g., mercury and copper; toxins, e.g., colicin; immunity; prototrophy in an auxotrophic host, e.g., uracil, leucine, histidine, tryptophan, etc.

In addition, there will be transcriptional and translational initiation and termination regulatory sequences. These sequences may be available from a wide variety of genes, where the untranslated upstream and downstream domains or regions may be employed as a source for the necessary regulatory sequences. Of particular interest is the use of yeast as a host, where various transcriptional initiation regions may be employed such as the transcriptional initiation regions of yeast glycolytic enzymes, e.g., glyceraldehyde-3-phosphate dehydrogenase, alcohol dehydrogenase, phosphoglucoisomerase, triosephosphate isomerase, phosphofructokinase, pyruvate kinase, phosphoglycerokinase, glucose-6-phosphate dehydrogenase, or the like; acid phosphatase; galactokinase; heat shock proteins; metallothionein; etc.

The regions will generally range from about 200 to 1000 bp, more usually about 200 to 600 bp, and may extend into the coding region of the particular structural gene associated with the transcriptional initiation region. To that extent, the 5'-terminus of the peptidase inhibitor structural gene may include from zero to ten, more usually from zero to five, conveniently one to three codons of the structural gene associated with the regulatory region. Since the first codon will be the methionine initiation codon, the difference between the subject peptidase inhibitors and the wild-type peptidase inhibitors will involve the substitution of the first codon for methionine or presence of one or more codons, usually not more than about five, inserted between the methionine initiation codon and the second codon of the wild-type peptidase inhibitor $\alpha_1$-antitrypsin. The transcriptional initiation region will normally include the sequences necessary for translational initiation as well. Thus, by employing the region involving transcriptional initiation, one also provides for translational initiation and expression.

The transcriptional initiation region can be selected or modified, so as to be constitutive or regulated. Thus, one can choose a promoter which provides for constitutive transcription of the structural gene. Alternatively, one can select a promoter or modify a promoter to provide for induced or controlled expression of the structural gene.

The promoter region of yeast glycolytic enzymes structural genes, as well as other structural genes, appears to be divided into two domains, one domain proximal to the structural gene which involves the binding of RNA polymerase and initiation of transcription, and a second domain distal to the structural gene which provides for enhanced efficiency of transcription and/or regulation. Therefore, by modifying the nucleotides beginning at about from about 300 to 500 nucleotides upstream from the initiation of the structural gene and extending at least to 200 nucleotides and usually 300 nucleotides or more in the upstream direction, one can modify the manner of expression. Thus, one can introduce at this site, sequences associated with regulation, such as the regulatory regions for such structural genes as GAL1, PHO5, or GAL110 or one can use temperature-sensitive regulatory regions, which regions may include the RNA polymerase binding domain. With these regions, one would employ a host which had the associated mechanism for regulation of the particular region.

The termination region will be at least about 200 nucleotides and may be 300 or more and can be conveniently derived from the same structural gene as the promoter or a different structural gene. It is found that the termination region and initiation regions should be balanced, since strong promoters appear to require strong terminators for efficacy. Therefore, for the most part, terminators will be chosen from structural genes which have similar levels of expression in the host as the structural gene associated with the transcriptional initiation region.

Where a cassette is available providing for transcriptional initiation and termination and one or more restriction sites intermediate the two regions, the subject structural genes may be inserted downstream from the transcriptional and translational initiation region, so as to be under the regulatory control of this domain, and followed by the termination region. Alternatively, one can join the various fragments to provide a construct comprising the transcriptional and translational initiation region, the structural gene having its initiation codon, and the transcriptional and translational termination region, which may then be introduced into an appropriate site of a vector having the appropriate replication system(s) and markers.

In order to provide for the modified polypeptides of the subject invention, a variety of techniques may be employed for providing the varied codons necessary for producing the modified polypeptide. One technique is in vitro mutagenesis. In this technique, a single strand of the structural gene or fragment thereof may be cloned in a single-stranded virus, DNA or RNA. A primer is then hybridized to the single-stranded virus containing the structural gene of the $\alpha_1$-antitrypsin, where the primer differs from the natural strand in the nucleotides to provide for the modified codon(s). Usually, the primer will have at least about ten nucleotides, more usually at least about 15 nucleotides and usually fewer than 50 nucleotides, more usually fewer than about 40 nucleotides, conveniently from about 25 to 35 nucleotides. Conveniently the virus M13 may be employed containing the $\alpha_1$-antitrypsin structural gene or fragment thereof, which fragment includes the active site. Particularly, where there are convenient available restriction sites bordering the active site, this fragment may be employed for mutagenesis, followed by joining to the other fragments to create the modified serine protease inhibitor. Mutagenized phage may then be detected and isolated employing the mutagenic primer as a probe and as appropriate, the fragment may be joined to the other fragments or where the entire gene was employed, the entire gene may be inserted into the vector. Conveniently, one may digest the M13 replicative form DNA so as to provide for double-stranded DNA.

Instead of using in vitro mutagenesis, one can employ chemical DNA synthesis, where the mutagenized sequence is synthesized and may then be inserted between the $\alpha_1$-antitrypsin 5' and 3' fragments to complete the gene. Again, one would choose or create convenient restriction sites for insertion, where desirably at least one of the sites should provide for a cohesive terminus. Other techniques may also prove to be useful, as appropriate.

The final construct will include from one to two replication systems of different unicellular microorganisms, e.g., bacterial and yeast; from zero to three markers, preferably from one to two markers, at least one common marker or one marker for each host for each replication system, and a cassette comprising a transcriptional initiation regulatory domain, followed downstream in the direction of transcription by the structural gene encoding for the modified serine peptidase inhibitor, followed by an appropriate termination system. This construct may then be used for introduction into an appropriate host, e.g., yeast. Various techniques are available for transforming the host with the DNA construct, where spheroplasts may be employed with polyethylene glycol precipitated DNA, conjugation, transfection, transduction, or the like.

The transformed host may then be grown in an appropriate selective medium. While the exemplified construct does not involve the use of a leader sequence allowing for secretion, such a construct could be produced whereby the peptidase inhibitor would be secreted and isolated from the nutrient medium. See, for example, U.S. Pat. Nos. 4,336,336; 4,338,397; and 4,411,994. See also U.S. patent application Ser. No. 522,909, filed Aug. 12, 1983. Alternatively, where the peptidase inhibitor is not secreted, the cells may be grown to high density, and where the expression is inducible, expression induced, followed by harvesting of the cells, lysing and isolating their desired product by conventional techniques. These techniques include extraction, chromatography, electrophoresis, or the like.

The subject serine peptidase inhibitors are shown to have specific inhibitory activity toward elastase, as well as inhibitory activity toward other serine peptidases. The compositions have a minimum activity as compared to conventional elastase assays where inhibition by human $\alpha_1$-antitrypsin is being measured of at least 25%, usually at least 35%, and desirably at least 50% of the $\alpha_1$-antitrypsin (Met). The compositions are resistant to oxidation as compared to the naturally occurring active site containing methionine.

For use in in vivo therapy, the subject compositions may be formulated in a variety of ways. Conveniently, the formulations may be liquid formulations involving deionized water, phosphate buffered saline, pH 7-7.5, or other physiologically acceptable medium. Usually, the composition will be administered by injection, either intraarterially or intravenously, or by inhalation employing an aerosol. Any dosage would depend on the manner of administration, the condition being treated, the frequency of administration, and the like, and would be comparable to the administration of enzyme inhibitory proteins, e.g., antibodies.

The subject compositions can be used for affinity chromatography for isolating leukocyte elastase, by binding the subject compositions to an appropriate solid substrate, which may then be used in a column. Samples suspected of containing elastase may then be introduced into the column and eluted. By adding strong nucleophiles (e.g., hydroxylamine or hydrazine) to the eluting solution, the complex between the elastase and the subject serine peptidase inhibitors may be broken and the elastase eluted. Alternatively, various assays may be devised, whereby conjugating the subject inhibitors with a haptenic ligand of interest, the resulting conjugate may still retain inhibitory activity, which is lost when antibody to the hapten binds to the conjugate.

The following examples are offered by way of illustration and not by way of limitation.

EXPERIMENTAL

All DNA manipulations were done according to standard procedures. See *Molecular Cloning*, T. Maniatis et al., Cold Spring Harbor Lab., 1982. Enzymes used in cloning were obtained either from New England Biolabs or Bethesda Research Laboratories and employed according to the supplier's directions. Yeast were transformed and grown using a variety of media including selective medium (yeast nitrogen base supplemented with amino acids, etc.) as appropriate but without leucine, YEPD medium, containing 2% (w/v) glucose; and in the case of plating medium contained 2% (w/v) agar and for transformation 3% top agar.

Cloning of alpha-1-antitrypsin.

A cDNA library was made from 10 μg of polyA+ RNA isolated from a part of a human liver. (Unless otherwise indicated $\alpha_1$-antitrypsin is from a human source.) This library was prepared by oligo-dT priming of the first cDNA strand and self-priming of the second cDNA strand. The ds cDNA was size fractionated on a Sepharose CL4B column and those molecules greater than 300 bp isolated. This fraction was treated with nuclease S1 and tailed with dCTP, using terminal transferase. The tailed cDNA was annealed to pBR322 which had been digested with PstI and tailed with dGTP. Transformation of *E. coli* HB101 yielded 60,000 colonies, where greater than 90% of the clones were recombinant.

Two synthetic oligonucleotide probes were used to isolate the alpha-1-antitrypsin ($\alpha_1$-AT) cDNA, the first probe corresponding to amino acid residues 344–350 near the C-terminus of the protein was used to probe 5,000 colonies and the second probe, corresponding to amino acid residues −23 to −17 (+1 being the first nucleotide of the first codon of the mature α₁-AT) of the signal peptide, was used to probe 25,000 colonies. The probe sequences were taken from the partial nucleotide sequence described by Kurachi et al., *Proc. Natl. Acad. Sci. USA* (1981) 78:6826; Leicht et al., *Nature* (1982) 297:655). Approximately 3% of the colonies hybridized to the C-terminal probe and four hybridized to the N-terminal probe. The four N-terminal clones and 12 C-terminal clones were isolated and subjected to restriction analysis. From these, three overlapping clones which cover the entire cDNA were subjected to further study and were used to construct the full-length cDNA clone.

The entire sequence of a composite full length cDNA derived from the three plasmids is as follows:

```
                                                                    −24
                                                                    Met Pro Ser Ser
                                            GGGGGGGGGGGAGGGTAATCGACA ATG CCG TCT TCT

−20                                    −10                                    −1
     Val Ser Trp Gly Ile Leu Leu Leu Ala Gly Leu Cys Cys Leu Val Pro Val Ser Leu Ala
     GTC TCG TGG CGC ATC CTC CTG CTG GCA GGC CTG TGC TGC CTG GTC CCT GTC TCC CTG GCT

1 Glu Asp Pro Gln Gly Asp Ala Ala Gln Lys Thr Asp Thr Ser His His Asp Gln Asp His
   1 GAG GAT CCC CAG GGA GAT GCT GCC CAG AAG ACA GAT ACA TCC CAC CAT GAT CAG GAT CAC
         — — — — — BamHI

21 Pro Thr Phe Asn Lys Ile Thr Pro Asn Leu Ala Glu Phe Ala Phe Ser Leu Tyr Arg Gln
  61 CCA ACC TTC AAC AAG ATC ACC CCC AAC CTG GCT GAG TTC GCC TTC AGC CTA TAC CGC CAG

41 Leu Ala His Gln Ser Asn Ser Thr Asn Ile Phe Phe Ser Pro Val Ser Ile Ala Thr Ala
 121 CTG GCA CAC CAG TCC AAC AGC ACC AAT ATC TTC TTC TCC CCA GTG AGC ATC GCT ACA GCC

61 Phe Ala Met Leu Ser Leu Gly Thr Lys Ala Asp Thr His Asp Glu Ile Leu Glu Gly Leu
 181 TTT GCA ATG CTC TCC CTG GGG ACC AAG GCT GAC ACT CAC GAT GAA ATC CTG GAG GGC CTG

81 Asn Phe Asn Leu Thr Glu Ile Pro Glu Ala Gln Ile His Glu Gly Phe Gln Glu Leu Leu
 241 AAT TTC AAC CTC ACG GAG ATT CCG GAG GCT CAG ATC CAT GAA GGC TTC CAG GAA CTC CTC

Arg(a,c)                                       Asp Gly(c)
 101 His Thr Leu Asn Gln Pro Asp Ser Gln Leu Gln Leu Thr Thr Gly Asn Gly Leu Phe Leu
 301 CAT ACC CTC AAC CAG CCA GAC AGC CAG CTC CAG CTG ACC ACC GGC AAT GGC CTG TTC CTC

121 Ser Glu Gly Leu Lys Leu Val Asp Lys Phe Leu Glu Asp Val Lys Lys Leu Tyr His Ser
 361 AGC GAG GGC CTG AAG CTA GTG GAT AAG TTT TTG GAG GAT GTT AAA AAG TTG TAC CAC TCA

141 Glu Ala Phe Thr Val Asn Phe Gly Asp Thr Glu Glu Ala Lys Lys Gln Ile Asn Asp Tyr
 421 GAA GCC TTC ACT GTC AAC TTC GGG GAC ACC GAA GAG GCC AAG AAA CAG ATC AAC GAT TAC

161 Val Glu Lys Gly Thr Gln Gly Lys Ile Val Asp Leu Val Lys Glu Leu Asp Arg Asp Thr
 481 GTG GAG AAG GGT ACT CAA GGG AAA ATT GTG GAT TTG GTC AAG GAG CTT GAC AGA GAC ACA

181 Val Phe Ala Leu Val Asn Tyr Ile Phe Phe Lys Gly Lys Trp Glu Arg Pro Phe Glu Val
 541 GTT TTT GCT CTG GTG AAT TAC ATC TTC TTT AAA GGC AAA TGG GAG AGA CCC TTT GAA GTC

Ala(b)
 201 Lys Asp Thr Glu Glu Glu Asp Phe His Val Asp Gln Val Thr Thr Val Lys Val Pro Met
 601 AAG GAC ACC GAG GAA GAG GAC TTC CAC GTG GAC CAG GTG ACC ACC GTG AAG GTG CCT ATG
                                                  — — — — — — BstEII

221 Met Lys Arg Leu Gly Met Phe Asn Ile Gln His Cys Lys Lys Leu Ser Ser Trp Val Leu
 661 ATG AAG CGT TTA GGC ATG TTT AAC ATC CAG CAC TGT AAG AAG CTG TCC AGC TGG GTG CTG

Asn(c)
 241 Leu Met Lys Tyr Leu Gly Asn Ala Thr Ala Ile Phe Phe Leu Pro Asp Glu Gly Lys Leu
 721 CTG ATG AAA TAC CTG GGC AAT GCC ACC GCC ATC TTC TTC CTG CCT GAT GAG GGG AAA CTA

261 Gln His Leu Glu Asn Glu Leu Thr His Asp Ile Ile Thr Lys Phe Leu Glu Asn Glu Asp
 781 CAG CAC CTG GAA AAT GAA CTC ACC CAC GAT ATC ATC ACC AAG TTC CTG GAA AAT GAA GAC
                                 — — — — — EcoRV

281 Arg Arg Ser Ala Ser Leu His Leu Pro Lys Leu Ser Ile Thr Gly Thr Tyr Asp Leu Lys
 841 AGA AGG TCT GCC AGC TTA CAT TTA CCC AAA CTG TCC ATT ACT GGA ACC TAT GAT CTG AAG

Val(a,c)
 301 Ser Ile Leu Gly Gln Leu Gly Ile Thr Lys Val Phe Ser Asn Gly Ala Asp Leu Ser Gly
 901 AGC ATC CTG GGT CAA CTG GGC ATC ACT AAG GCT TTC AGC AAT GGG GCT GAC CTC TCC GGG

321 Val Thr Glu Glu Ala Pro Leu Lys Leu Ser Lys Ala Val His Lys Ala Val Leu Thr Ile
 961 GTC ACA GAG GAG GCA CCC CTG AAG CTC TCC AAG GCC GTG CAT AAG GCT GTG CTG ACC ATC

341 Asp Glu Lys Gly Thr Glu Ala Ala Gly Ala Met Phe Leu Glu Ala Ile Pro  Met Ser  Ile
1021 GAC GAG AAA GGG ACT GAA GCT GCT GGG GCC ATG TTT TTA GAG GCC ATA CCC  ATG TCT  ATC
```

-continued

```
361 Pro Pro Glu Val Lys Phe Asn Lys Pro Phe Val Phe Leu Met Ile  Glu Gln Asn Thr Lys
1081 CCC CCC GAG GTC AAG TTC AAC AAA CCC TTT GTC TTC TTA ATG ATT GAA CAA AAT ACC AAG
     - - -- - - AvaI

381 Ser Pro Leu Phe Met Gly Lys Val Val Asn Pro Thr Gln Lys OC
1141 TCT CCC CTC TTC ATG GGA AAA GTG GTG AAT CCC ACC CAA AAA TAA CTGCCTCTCGCTCCTCAAC
                                                         ----- HinfI

AAT CCC ACC CAA AAA TAG
```

LEGEND

Nucleotide and predicted amino acid sequences of $\alpha_1$-AT cDNA. The reactive center met—ser at positions 358–359 is boxed. Subscripts to amino acids in parentheses identify differences between the subject protein sequence and those derived from (a) protein sequencing (Carrell et al., 1982), (b) the cDNA of Woo et al., [see Carrell et al., 1982]), and (c) the cDNA of Bollen et al., 1983. The synthetic DNA molecules used in the construction of the BamHI to SalI fragment encoding the mature protein are shown as are the cDNA restriction sites used in this construction.

The above sequence was determined using the dideoxy sequencing method of Sanger et al., *Proc. Natl. Acad. Sci. USA* (1977) 74:5463, in the M13 vectors of Messing et al., *Nucleic Acids Res.* (1981) 9:309. The differences at the nucleotide and amino acid level from the published cDNA sequences are shown.

Construction of the full length clone for expression of yeast began with three fragments isolated from cDNA clones: (1) a 630 bp BamHI-BstEII fragment;(2) a 450 bp BstEII-AvaI fragment; and (3) an 85 bp AvaI-HinfI fragment. A synthetic adapter was employed having the following sequence:

$$A_2TC_3AC_3A_5TAG$$
$$G_3TG_3T_5ATCAGCT$$

Approximately two pmoles of fragments 1 and 2 were ligated together and after removal of the ligase, digested with BamHI and AvaI. Fragment 3 and the synthetic adapter were ligated and digested with AvaI and SalI and the two resulting fragment mixtures were ligated followed by digestion with BamHI and SalI. Fragments migrating upon electrophoresis in the region of about 1000-1400 bp were isolated and cloned by substitution into BamHI and SalI digested and alkaline phosphatase treated pBR322. The resulting plasmid is referred to as pATi.

Mutagenesis of alpha-1-antitrypsin (ATi).

The PvuII-SalI fragment of the $\alpha_1$-antitrypsin cDNA, described previously, coding for amino acids 238 to 394 was cloned by SmaI-SalI substitution into M13 mp10 (Messing, *Methods in Enzymology* 101 part C, 20–78, (Eds. Wu, Grossman and Moldave) Academic Press (1983)). Single stranded viral DNA was isolated and used as a template for site directed mutagenesis as described in Zoller and Smith, *Nucleic Acid Research* (1982) 10:6487–6500; Brake et al., *Proc. Natl. Acad. Sci. USA* (1984) (described in U.S. patent application Ser. No. 522,909, filed Aug. 12, 1983), using a synthetic 30 mer as a mutagenic primer. This primer of sequence 5' GACCTCGGGGGGGATAGACACGG-GTATGGC3' was used to prime second strand synthesis on single-stranded M13 mp 10 containing the wild-type $\alpha_1$-antitrypsin fragment. The mismatch between wild-type fragment and primer is underlined in the primer sequence. Mutagenized phage were located using the same primer as a probe in hybridization experiments (Ish-Horowicz and Burke, supra) and hybridized filters were washed for 60 min at 65° C. in 0.15 M NaCl, 15 mM sodium citrate. Single-stranded recombinant M13 mp10 was prepared from the positive phage plaques and the codon change in the $\alpha_1$-antitrypsin fragment was confirmed by sequencing.

Construction of pC1/1PHO5ATi(Val) and pC1/1PHO5ATi(Met).

Yeast expression plasmids containing the mutant $\alpha_1$-antitrypsin gene (pC1/1PHO5ATi(Val)) or the wild-type $\alpha_1$-antitrypsin gene (pC1/1PHO5ATi(Met)) under control of the PHO5 promoter and GAPDH terminator were constructed.

Plasmid pC1/1PHO5ATi(Val) was constructed as follows. A 360 bp EcoRV-SalI fragment coding for amino acids 271 to 394 and containing the valine mutation was obtained by EcoRV-SalI digestion of double-stranded M13 of the positively identified phage plaques containing the $\alpha_1$-antitrypsin mutated fragment. This fragment was ligated to the 1350 bp BamHI-EcoRV fragment containing the PHO5 promoter and N-terminal residues of $\alpha_1$- antitrypsin, prepared from pPHO5ATi, and to the ca. 1000bp SalI-BamHI GAPDH terminator fragment prepared from pPGAP. After ligation, the mixture was digested with BamHI prior to ligation into BamHI cut and alkaline phosphatase treated pC1/1. After transformation of *E. coli* HB101 one positive clone corresponding to pC1/1PHO5ATi(Val) was obtained after restriction analysis of plasmid DNA from 12 clones, with the orientation of ATi expression in the clockwise direction, with amp$^r$ being counterclockwise.

Plasmid pC1/1PHO5ATi(Met) was constructed as follows. The BamHI-SalI 1800 bp fragment containing the PHO5 promoter and the wild-type $\alpha_1$-antitrypsin gene was prepared from pPHO5ATi. This fragment was ligated to the ca. 1000 bp SalI-BamHI GAPDH terminator fragment prepared from pPGAP. After ligation, the mixture was digested with BamHI prior to ligation into BamHI cut and alkaline phosphatase treated pC1/1 to produce pC1/1PHO5ATi(Met), with the orientation of ATi expression in the clockwise direction, with amp$^r$ being counter-clockwise.

Plasmid pPHO5ATi was obtained as follows. The PHO5 gene was isolated from a yeast genomic library employing an oligonucleotide probe 5' GGCACT-CACACGTGGGACTAG3' derived from the published partial sequence (Meyhack et al., *The EMBO Journal* (1982) 1:675–680). A subfragment of this clone containing 550 bp of the 5'-untranslated region and approximately 80 bp of coding sequence was subcloned as a BamHI-SalI substitution in pBR322 to provide pPHO5. This fragment has the sequence 5' ATGTT-TAAA3', encoding the first three amino acids, the second and third codons specifying an AhaIII site. pPHO5 was digested with BamHI and AhaIII. The resulting 550 bp fragment was isolated by gel electrophoresis and ligated to a (BamHI)-SalI fragment isolated from pATi which contains the $\alpha_1$-antitrypsin gene to produce a 17. kb BamHI-SalI fragment. To obtain the (BamHI)-SalI fragment, pATi was digested with BamHI, the ends were blunted with Klenow, and the plasmid was subsequently digested with SalI. The (BamHI)-SalI fragment was purified by gel electrophoresis. The 1.7 kb BamHI-SalI fragment containing the $\alpha_1$-antitrypsin gene and PHO5 promoter was substituted into BamHI-SalI and alkaline phosphatase treated pBR322 to produce pPHO5ATi.

Plasmid pPGAP was constructed as described under construction of pC1/1GAPATi(Val) and pC1/1GAPATi(Met).

Plasmid pC1/1 is a derivative of pJDB219 (Beggs, Nature (1978) 275:104) in which the region corresponding to bacterial plasmid pMB9 in pJDB219 has been replaced by pBR322 in pC1/1.

Plasmids pC1/1PHO5ATi(Val) or pC1/1PHO5ATi(Met) were transformed in S. cerevisiae AB103.1(MATα, leu2-3,112, ura3-52, pep4-3, his4-580, [cir°]) Cells were grown in leucine⁻ selective medium in high or low phosphate.

Construction of pC1/1GAPATi(Val) and pC1/1GAPATi(Met).

Yeast expression plasmids containing the mutant $\alpha_1$-antitrypsin gene (pC11GAPATi(Val)) or the wild-type $\alpha_1$-antitrypsin gene (pC1/1GAPATi(Met)) under control of the GAPDH promoter and terminator were constructed.

Plasmid pC1/1GAPATi(Val) was constructed as follows. A 600 bp fragment corresponding to the 5' end of the $\alpha_1$-antitrypsin gene was obtained by digesting pPGAPATi with NcoI and BstEII and subsequent purification by gel electrophoresis. A second fragment of 470 bp corresponding to the 3' end, including the active region of the mutagenized $\alpha_1$-antitrypsin gene, was obtained by digesting pC1/1PHO5ATi(Val) with BstEII and SalI and further purification by gel electrophoresis. Both fragments were ligated together, and the resulting 1070 bp NcoI-SalI fragment containing the valine mutation was cloned into pPGAP, which had been previously digested with NcoI and SalI and treated with alkaline phosphatase. The resulting plasmid, pPGAPATi(Val) was digested with BamHI and blunt-ending, SalI digestion and treatment with alkaline phosphatase. The NcoI-SalI fragment was substituted with an approximately 1250bp blunt-ended (BamHI)-SalI fragment obtained from plasmid pATi by BamHI digestion, blunt ending and SalI digestion. This fragment was inserted in the pPGAP vector to produce plasmid pPGAPATi.

Plasmid pC1/1PHO5ATi(Val) was obtained as described previously.

A yeast expression vector was prepared called pPGAP having a polyrestriction site linker between the GAPDH terminator and a truncated GAPDH promoter region.

Plasmids pGAP2 and pGAP1 were obtained as follows: A yeast gene library was prepared by inserting fragments obtained after partial digestion of total yeast DNA with restriction endonuclease Sau3A in lambda-phage Charon 28 (Blattner et al., Science (1977) 196:161–169). The phage library was screened with DNA complementary to the yeast GAPDH mRNA and the yeast GAPDH gene GAP49 (Holland and Holland, J. Biol. Chem. (1979) 254:5466–5474) from one of these clones was subcloned as either an about 3.3 kb BamHI fragment in the BamHI site of pBR322 (pGAP-2) or as an about 2.1 kb HindIII fragment in the HindIII site of pBR322 (pGAP-1). After digestion of the plasmid pGAP1 with HinfI, a 500 bp fragment was gel isolated, the fragment resected with Bal31 to remove about 50 bp, ligated with HindIII linkers, followed by digestion with HindIII and the resulting about 450 bp fragment inserted into the HindIII site of pBR322 after treatment of the plasmid with alkaline phosphatase. The resulting plasmid pGAP128 was digested with HindIII, the fragment made blunt-ended with the Klenow fragment of DNA polymerase I and nucleoside triphosphates and the resulting blunt-ended about 450 bp fragment gel isolated, inserted into the SmaI site of plot5 after SmaI digestion and alkaline phosphatase treatment to provide the plasmid plot5 pGAP128 which contained about −400 to +27 of the GAPDH coding region. plot5 was prepared by inserting the 40 bp polylinker fragment of the following sequence

```
       EcoRI          BamHI              BglII   XbaI
         |              |                  |       |
5'  AATTCCCGGGGATCCGTCGACCTGCAGATCTCTAGAAGCTCCAG
3'      GGGCCCCTAGGCAGCTGGACGTCTAGAGATCTTCGAGGTC
                       |                  |              |
                      SalI              PstI          PvuII
``` the 2.6 kb fragment containing the GAPDH expression cassette with the valine-$\alpha_1$-antitrypsin gene, was purified by gel electrophoresis and inserted into BamHI and alkaline phosphatase treated pC1/1. The plasmid pC1/1GAPATi(Val) was obtained with the orientation of ATi expression in the counterclockwise direction, the same as amp$^r$.

Plasmid pC1/1GAPATi(Met) was constructed as follows (see copending application Ser. No. 609,540, filed May 11, 1984, whose disclosure is incorporated herein by reference). The BamHI 2.6 kb fragment containing the GAPDH promoter and terminator and wild-type $\alpha_1$-antitrypsin gene was prepared from pGAPATi. This fragment was ligated to BamHI and alkaline phosphatase treated pC1/1 to produce pC1/1GAPATi(Met) with the orientation of ATi expression in the counterclockwise direction, the same as amp$^r$.

Plasmid pGAPATi was constructed as follows. Plasmid pPGAP was digested with NcoI, followed by into pBR322 as an EcoRI-PvuII substitution followed by insertion of the trp-lac (tac) promoter (Russell and Bennett, Gene (1982) 20:231–245) into the PvuII site with transcription oriented toward the polylinker sequence. Plasmid plot5pGAP128 was then digested with BamHI and TaqI to yield an approximately 390 bp BamHI-TaqI fragment having the −400 to −26 bp of the GAPDH promoter. The BamHI-TaqI fragment was ligated to a synthetic fragment having the following sequence:

| $CGA_2TA_3(CA)_3TA_3CA_3CACCATG_3A_2T_2CGT_2AG_2$ |
| $T_2AT_3(GT)_3AT_3GT_3GTGGTAC_3T_2A_2GCA_2TC_2AGCT$ | and containing −26 to 1 bp of the GAPDH promoter and an NcoI site. The resulting BamHI-SalI fragment, which was digested with BamHI and SalI and used to replace the BamHI-SalI fragment of BamHI-SalI digested pBR322 treated with alkaline phosphatase. After ligation, the plasmid pGAPNRS was obtained which was digested with BamHI and SalI to provide a 400 bp BamHI-SalI fragment which was gel isolated. This fragment was ligated to a an about 1 kb SalI-BamHI fragment containing the GAPDH terminator region and a short segment of 3′ coding region and the resulting 1.4 kb BamHI-BamHI fragment digested with BamHI. The about 1 kb SalI-BamHI GAPDH terminator fragment was obtained by gel electrophoresis after SalI and BamHI digestion of pGAP2, prepared as previously described.

pBR322 was digested with EcoRI and SalI, the termini blunt-ended and ligated to BamHI linkers, followed by BamHI digestion and the BamHI-BamHI 3.8 kb fragment gel isolated, recircularized by self-ligation, cloned and designated pBRARl-Sal. The 1.4 kb BamHI-BamHI fragment was inserted into the BamHI-digested, alkaline phosphatase treated pBRARl-Sal vector to provide the plasmid pPGAP of about 5.3 kb with the orientation in the opposite direction of the amp$^r$.

Plasmids pC1/1GAPATi(Val) or pC1/1GAPATi(Met) were transformed in S. cerevisiae AB110 (Matα, ura3-52, leu2-04 or leu2-3,112, pep4-3, his4-580, [cir°]) The yeast cells were grown in leucine⁻ selective medium or in YEPD medium.

Anti-elastase activity and oxidation resistance of modified alpha-1-antitrypsin.

Yeast extracts were prepared by lysis with glass beads and centrifuged to remove cell debris (Valenzuela et al., Nature (1982) 298:347-350). The soluble cell proteins were analyzed by SDS polyacrylamide gels (Laemmli, Nature (1970) 227:680) and blotted onto nitrocellulose paper (Towbin et al., Proc. Natl. Acad. Sci. USA (1979) 76:4350-4355). $\alpha_1$-antitrypsinrelated proteins were visualized by washing the nitrocellulose paper with rabbit anti-$\alpha_1$-antitrypsin (Accurate Chemicals) followed by horseradish peroxidase/goat antirabbit antibody staining. Results of the gel analysis showed that a protein of 42,000 daltons is specifically induced in transformants containing the wild-type (Met) or mutant (Val) $\alpha_1$-antitrypsin cDNA. This protein reacts with anti-$\alpha_1$-antitrypsin.

To determine the anti-elastase activities of the mutant (Val) or wild-type (Met) $\alpha_1$-antitrypsin, appropriate yeast extracts were incubated with human leukocyte elastase (HLE) and a synthetic peptide substrate the cleavage of which can be assayed at 410 nm (Beatty et al., supra). For the assay, extracts were diluted in 50 mM Tris pH8, 50 mM NaCl. Aliquots were transferred to tubes containing 0.1 mM Meo-Suc-Ala-Ala-Pro-Val-p-nitroanilide (Vega), 50 mM Tris pH8, 0.5M NaCl, 100 μg BSA (bovine serum albumin), in a volume of 1 ml. Assays were initiated by the addition of 0.1 5 μg HLE and were incubated for 15 min at 28° C., terminated by the addition of 100 μl of 8N acetic acid and the absorbance at 410 nm determined (Beatty et al., supra). Protein concentrations were determined as described in Bradford, Anal. Biochem. (1976) 72:248-253. From the amount of human leukocyte elastase activity observed, given the protein concentration of the yeast extracts and the amount of the enzyme added, the percentage of the yeast soluble protein which is $\alpha_1$-antitrypsin can be calculated. It is assumed that there is 100 percent human leukocyte elastase activity, a 1:1 complex between human leukocyte elastase and $\alpha_1$-antitrypsin whose molecular weights are 29 kD and 42 kD, respectively. In the experiment shown in Table 1 $\alpha_1$-antitrypsin is 3.0 to 3.5 percent in the Met extract (assays 7 and 8) and 2.3 to 2.6 percent in the Val extract (assays 9 and 10). In Table 2, $\alpha_1$-antitrypsin is 5.3% in the Met extract (assay 4) and 3.8 percent in the Val extract (assay 6).

To determine if the valine-$\alpha_1$-antitrypsin was oxidation resistant, extracts were treated with N-chlorosuccinimide (NCS) which converts susceptible methionines to their sulphoxides (Johnson and Travis, J. Biol. Chem. (1978) 253:7142-7144). For this purpose, aliquots of the extracts were diluted in 50 mM Tris pH8, 50 mM NaCl, incubated at room temperature for 5 min in 100 μl of 50 mM Tris pH8, with the indicated amount of NCS, and assayed for anti-HLE activity.

Table 1 and Table 2 show results obtained with wild-type (Met) or mutant (Val) $\alpha_1$-antitrypsin using pC1/1PHO5ATi vectors and pC1/1GAPATi vectors, respectively.

TABLE 1

Effects of NCS Oxidation of $\alpha_1$-antitrypsin Activity in Yeast Extracts Assayed by Inhibition of Elastase Activity Using pC1/1PHO5ATi(Val) or pC1/1PHO5ATi(Met)

| Assay No. | Plasmid | Vol. of Yeast Extract$^a$ | μg $\alpha_1$AT$^b$ | NCS (10 mM) | Elastase Activity (%) |
|---|---|---|---|---|---|
| 1 | — | — | — | — | 100 |
| 2 | — | — | 0.1 | — | 85 |
| 3 | — | — | 0.2 | — | 67 |
| 4 | — | — | 0.5 | — | 22 |
| 5 | — | — | 1.0 | — | 0 |
| 6 | Cl/1 | 1.5 μl | — | — | 100 |
| 7 | Met | 0.5 μl | — | — | 54 |
| 8 | Met | 1.5 μl | — | — | 8 |
| 9 | Val | 0.5 μl | — | — | 52 |
| 10 | Val | 1.5 μl | — | — | 15 |
| 11 | — | — | 1.0 | — | 5 |
| 12 | — | — | 1.0 | 10 μl | 91 |
| 13 | Cl/1 | 3.8 μl | 1.0 | — | 12 |
| 14 | Cl/1 | 3.8 μl | 1.0 | 10 μl | 84 |
| 15 | Met | 1.5 μl | — | — | 8 |
| 16 | Met | 1.5 μl | — | 10 μl | 93 |
| 17 | Val | 1.5 μl | — | — | 20 |
| 18 | Val | 1.5 μl | — | 10 μl | 18 |

$^a$Protein concentrations are 6.4 mg/ml for Cl/1 extract, 8.0 mg/ml for Met extract and 9.7 mg/ml for Val extract.
$^b$Control human $\alpha_1$-antitrypsin.

TABLE 2

Effects of NCS Oxidation of $\alpha_1$-antitrypsin Activity in Yeast Extracts Assayed by Inhibition of Elastase Activity Using pC1/1GAPATi(Val) or pC1/1GAPATi(Met)

| Assay No. | Plasmid | Vol. of Yeast Extract$^a$ | μg $\alpha_1$AT$^b$ | NCS (10 mM) | Elastase Activity (%) |
|---|---|---|---|---|---|
| 1 | — | — | — | — | 100 |
| 2 | — | — | — | — | 99 |
| 3 | — | — | 1.0 | — | 10 |
| 4 | Met | 0.25 μl | — | — | 7 |
| 5 | Met | 0.5 μl | — | — | 6 |
| 6 | Val | 0.5 μl | — | — | 16 |
| 7 | Val | 1.0 μl | — | — | 13 |
| 8 | — | — | 0.5 | — | 44 |
| 9 | — | — | 0.5 | + | 96 |
| 10 | Met | 1.0 μl | — | — | 10 |
| 11 | Met | 1.0 μl | — | + | 53 |
| 12 | Val | 1.0 μl | — | — | 15 |
| 13 | Val | 1.0 μl | — | + | 15 |
| 14 | Val | 1.0 μl | 0.5 | — | 9 |
| 15 | Val | 1.0 μl | 0.5 | + | 15 |

$^a$Protein concentrations are 15.4 mg/ml for Met extract and 15.7 mg/ml for Val extract.
$^b$Control human $\alpha_1$-antitrypsin.

It is evident from the above results, that the subject modified polypeptides are effective inhibitors of human leukocyte elastase and strongly complex with the elastase. The subject-proteins can therefore find a wide variety of applications. Due to the substantially enhanced resistance, to oxidation, as evidenced by the reaction with the N-chlorosuccinimide with retention of activity, the subject compounds can find use in commercial applications, such as affinity chromatography. Furthermore, by virtue of their enhanced stability in vivo, the compounds may find use in therapies for lung disorders.

Although the foregoing invention has been described in some detail by way of illustration and example for purposes of clarity of understanding, it will be obvious that certain changes and modifications may be practiced within the scope of the appended claims.

What is claimed is:

1. An analog of human alpha-1-antitrypsin wherein the amino acid corresponding to the methionine at position 358 of wild-type alpha-1-antitrypsin is substituted with an aliphatic amino acid, said analog exhibiting human leukocyte elastase activity and resistant to oxidation by N-chlorosuccinimide.

2. The alpha-1-antitrypsin analog of claim 1 wherein said aliphatic amino acid is selected from the group consisting of alanine, valine, leucine, isoleucine, serine and threonine.

3. The alpha-1-antitrypsin analog of claim 2 wherein said aliphatic amino acid is valine.

4. The alpha-1-antitrypsin analog of claim 3 which corresponds in amino acid sequence to wild-type alpha-1-antitrypsin except fo position 358.

* * * * *